United States Patent [19]

Hara et al.

[11] Patent Number: 4,686,211

[45] Date of Patent: Aug. 11, 1987

[54] MEDICAL COMPOSITION FOR EXTERNAL APPLICATION

[75] Inventors: Kenji Hara, Utsunomiya; Hiromichi Takahashi, Kawasaki; Tetsuro Kamiya, Ichikaimachi; Kaoru Tsujii, Utsunomiya, all of Japan

[73] Assignee: Kao Corporation, Tokyo, Japan

[21] Appl. No.: 778,226

[22] Filed: Sep. 20, 1985

[30] Foreign Application Priority Data

Oct. 11, 1984 [JP] Japan .................................. 59-213152

[51] Int. Cl.$^4$ ............................................. A61K 31/66
[52] U.S. Cl. ..................................................... 514/148
[58] Field of Search ......................................... 514/148

Primary Examiner—Stanley J. Friedman
Attorney, Agent, or Firm—Oblon, Fisher, Spivak, McClelland & Maier

[57] ABSTRACT

A medical composition for external application comprises a dialkyl phosphate represented by the formula:

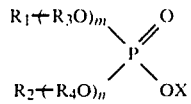

wherein $R_1$ and $R_2$ independently represent a hydrocarbon group having from 6 to 24 carbon atoms, $R_3$ and $R_4$ independently represent hydrocarbon group having from 2 to 6 carbon atoms, m and n independently represent a value of from 0 to 20, and x represents a hydrogen atom or a salt of an alkali metal and the like.

In the presence of the dialkyl phosphate, percutaneous intake of medically active ingredients is highly enhanced. Examples of the medically active ingredients directed to in the invention include antiinflammatory agents such as ethyl aminobenzoate; adrenocortical hormones such as hydrocortisone; etc.

The inventive composition is highly safe without giving any stimulation to the skin.

11 Claims, 2 Drawing Figures

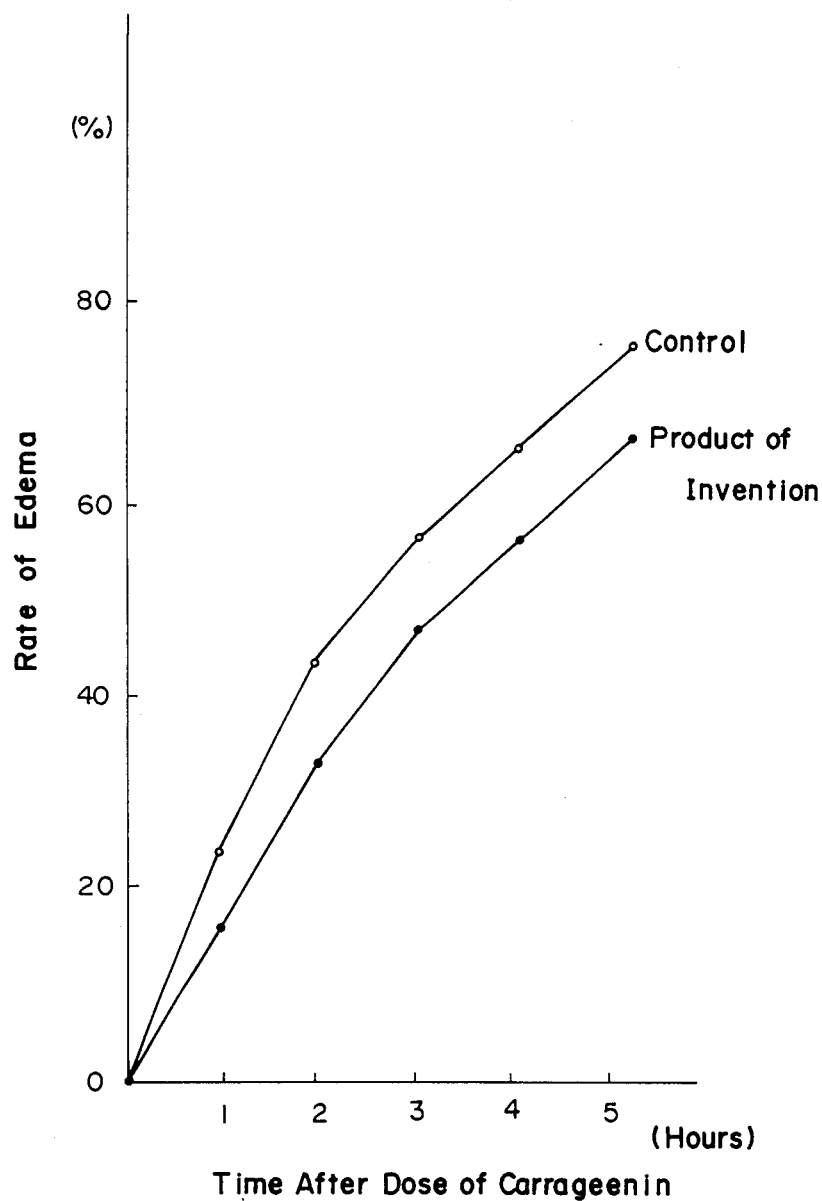

MEDICAL COMPOSITION FOR EXTERNAL APPLICATION

BACKGROUND OF THE INVENTION (i) Field of the Invention:

This invention relates to novel medical compositions for external applications.

(ii) Description of the Prior Art:

As is well known in the art, medicines have been ordinarily dosed by several ways, i.e. perorally, rectally or hypodermically, of which peroral administration is widely used. However, the peroral dosage involves the disadvantage that it may bring about adverse side effects such as gastroenteric trouble, inappetence, vomit, stomachache and the like, and that the efficacy is shown, in most cases, only on a large dosage of a medicine. For the purpose of overcoming the above disadvantage, external medicines being applied percutaneously have recently been developed as expected to more safely develop the pharmaceutical efficacy while lowering the side effects, and are, in fact, commercially sold. However, the percutaneous absorption of medical ingredients in the known external medicine is not always satisfactory and the above purpose has not been achieved well. This is because the horny layer of the skin, which constitutes the outermost layer, has the physiological function as a barrier against substances to be passed into the body, so that even if a base which is employed in ordinary external medicines is used along with medically effective ingredients, the ingredients are not percutaneously absorbed satisfactorily in most cases. Accordingly, it is necessary to cause the medical substances to be passed through the horny layer in order to enhance the percutaneous absorption of the medical substances.

To this end, it is general to add so-called percutaneous absorption enhancers to the base. For instance, there are known, as such enhancers, amide compounds such as dimethylsulfoxide, dimethylacetamide, dimethylformamide and N,N-diethyl-m-toluamide, azacycloalkane-2-one derivatives such as 1-dodecylazacycloheptan-2-one, esters of alcohols and carboxylic acids such as isopropyl myristate, isopropyl palmitate, diethyl sebacate, diisopropyl adipate and the like, and crotonyl-N-ethyl-o-toluidine.

However, these absorption enhancers have not the satisfactory absorption effect. If these enhancers are added to external medicines, the practical pharmaceutical effect may not be obtained. Alternatively, the absorption enhancers may irritate the skin and may attack synthetic resins because of the ability as strong solvent, so that irritative substances or sensitizing substances are eluted from the container for medicine or clothes. This will limit the application or use of the enhancer, thus presenting problems in practical application.

SUMMARY OF THE INVENTION

We made intensive studies in order to develop medical compositions for external application which enable medical substances to be percutaneously absorbed in high efficiency and which are highly safe against the skin. As a result, it was found that when a specific type of dialkyl phosphate was used in combination with medically effective ingredients, external medicine compositions which were free of the above disadvantages were obtained. The present invention is accomplished based on the above finding.

More specifically, the present invention provides a medical composition for external use which comprises medically effective ingredients and a dialkyl phosphate of the following general formula (I)

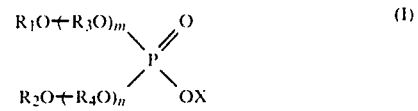

in which $R_1$ and $R_2$ independently represent a hydrocarbon group having from 6 to 24 carbon atoms, $R_3$ and $R_4$ independently represent a hydrocarbon group having from 2 to 6 carbon atoms, m and n independently represent a value of from 0 to 20, and X represents a hydrogen atom, or a salt of an alkaline metal, ammonium, alkanolammonium having 2 or 3 carbon atoms, alkylammonium having from 1 to 4 carbon atoms, basic amino acid or morpholine.

BRIEF DESCRIPTION OF THE DRAWINGS

FIG. 2 is a graph showing the inhibitory rate of edema in relation to time in a carrageenin edema-inhibiting test using rats.

DETAILED DESCRIPTION OF THE INVENTION AND PREFERRED EMBODIMENTS

Figure 1:
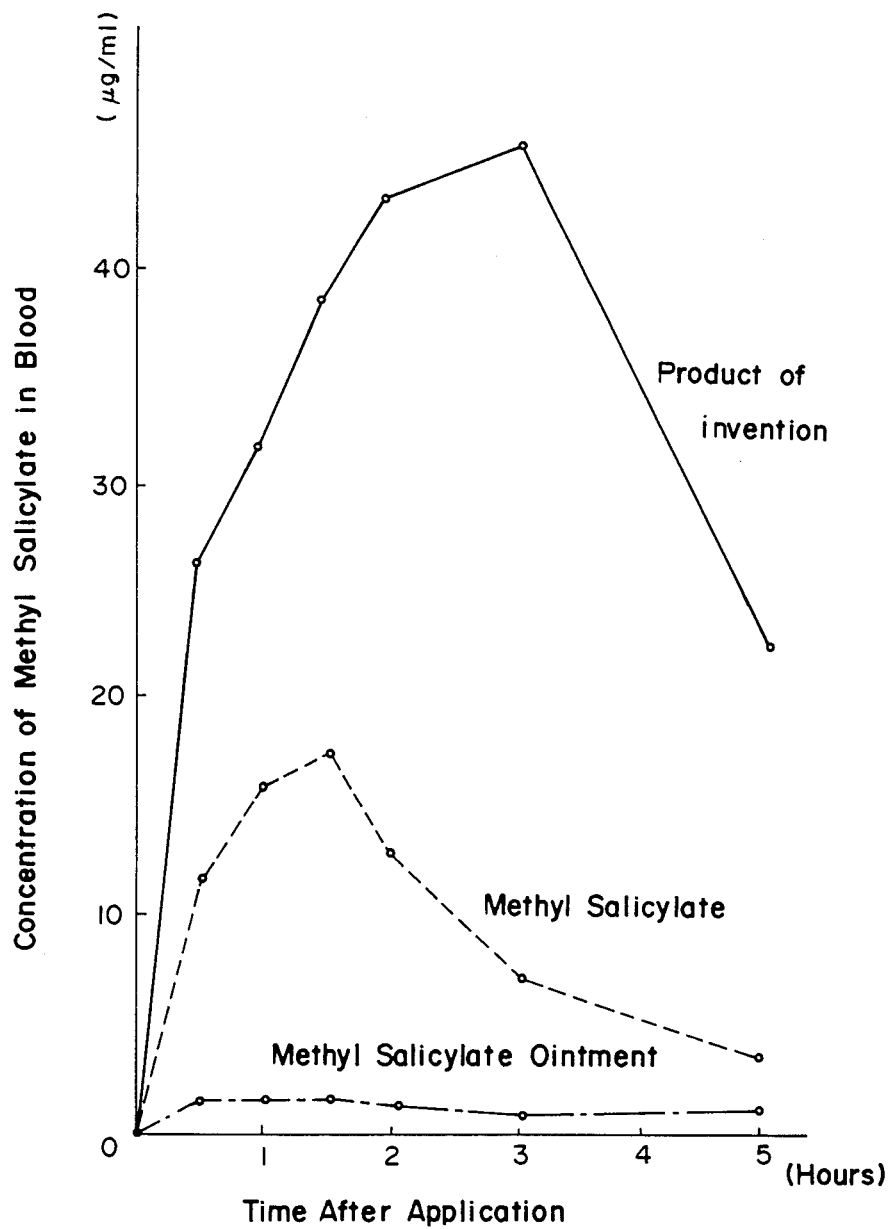
FIG. 1 is a graph of the concentration of methyl salicylate in blood in relation to time when salicylate external agents are applied to the abdomen of rabbits.

The dialkyl phosphate (I) used in the practice of the invention should preferably be in the form of salts. The alkaline metal which is represented by X in the formula (I) is sodium, potassium, lithium, rubidium, cesium or francium. On the other hand, the basic amino acid which is able to form a salt with the alkaline metal is, for example, lysine, arginine or histidine. This reason why the basic amino acid is preferred is due to the high stability. Moreover, the sum of m and n is preferred to be in the range of from 0 to 10. Most preferably, m and n are both zero. Most preferable and specific examples include didecyl phosphate arginine salt, didodecyl phosphate arginine salt, ditetradecyl phosphate arginine salt, dihexadecyl phosphate arginine salt, dioctadecyl phosphate arginine salt, dieicosyl phosphate arginine salt, didecyl phosphate lysine salt, didodecyl phosphate lysine salt, ditetradecyl phosphate lysine salt, dihexadecyl phosphate lysine salt, dioctadecyl phosphate lysine salt, dieicosyl phosphate lysine salt and the like.

The medically effective ingredients used in the present invention are not limited to specific ones but may be any ingredients ordinarily used for external application. Examples of ingredients whose absorption is promoted with an increasing efficacy include anodynes and anti-inflammatory agents such as ethyl aminobenzoate, dibucaine hydrochloride, tetracaine hydrochloride, procaine hydrochloride, lidocaine, methyl salicylate, guaiazulene, sodium guaiazulenesulfonate, aluminium chlorhydroxy allantoinate, bendazac, indomethacin, glycyrrhetinic acid, glycyrrhizinic acid, bufexamac, dextran sulfate sodium, crotamiton, butyl flufenamate, allantoin, aloe powder, ichthammol, dipotassium glycylrrhizinate, monoammonium glycyrrhizinate, stearyl glycyrrhetinate and hinokitiol; adrenocortical hormones such as hydrocortisone, hydrocortisone acetate, hydrocortisone butyrate, fluocinolone acetonide, fulmethasone pivalate, fluocinonide, fluorometholone, beclomethasone dipropionate, dexamethasone, dexamethasone acetate, fludroxycortide, betamethasone valerate, betamethasone dipropionate, triamcinolone acetonide, predonisolone, methylpredonisolone, methylpredonisolone acetate, difulcortolone valerate, clobetasole propionate, amcinonide, halcinonide, predonisolone valerate, hydrocortisone butyrate/valerate and the like, hormones such as estradiol, estrone, ethinylestradiol, diethylstilbestrol, hexoestrol and the like; antiseptics and sterilizers such as phenol, resorcinol, salicylic acid, hexachlorophene, mercurochrome, thimerosal, acrinol, iodine, benzalkonium chloride, benzethonium chloride, penicillin V, benzylpenicilline benzathine, streptomycin, chloramphenicol, tetracycline, tetracycline hydrochloride, erythromycin, fradiomycin, fradiomycin sulfate, bacitracin, oxytetracycline hydrochloride, kanamycin sulfate, kanamycin, chloromycetin, polymyxin B, nitrofurazone, potassium permanganate, boric acid, borax, benzoic acid, sodium benzoate, sodium salicylate, sorbic acid, potassium sorbate, dehydroacetic acid, sodium dehydroacetate, ethyl paraoxybenzoate, butyl paraoxybenzoate, propyl paraoxybenzoate, methyl paraoxybenzoate, isopropylmethylphenol, cresol, thymol, parachlorophenol, photosensitizer No. 101, photosensitizer No. 201, chloramine T, thianthol, lysozyme chloride, chlorhexidine hydrochloride, chlorhexidine gluconate, trichlorocarbanilide, 3-trifluoromethyl-4,4'-dichlorocarbanilide, hexachlorophene and the like; antihistaminic agents such as isothipendyl hydrochloride, diphenylimidazole, clemizole sulfate, diphenhydramine, diphenhydramine laurylsulfate, chlorpheniramine maleate and the like; antifugal agents such as chrysarobin, undecylenic acid, zinc undecylenate, pentachlorophenol, phenylmercuric acetate, thimerosal, trichomycin, tolunaftate, phenyliodoundecynoate, clotrimazole, haloprogine, variotin, pyrrolnitrin, siccanin, nystatin, exalamide, ciclopirox oramine, miconazole nitrate, econozole nitrate, isoconazole nitrate and the like; vitamins retinol, retinol acetate, retinol palmitate, dehydroretinol, ergocalciferol, dl-α-tocopherol, dl-α-tocopheryl acetate, dl-α-tocopherol/calcium succinate, ubiquinone, phytomenadione, menaquinone, menadione, thiamine hydrochloride, thiamine nitrate, thiamine phosphate, riboflavin, flavin mononucleotide, riboflavin butyrate, pyridoxine hydrochloride, pyridoxale 5'-phosphate, pyridoxine dicaprylate, pyridoxine dipalmitate, pyridoxine tripalmitate, cyanocobalamin, hydroxycobalamin, deoxyadenosylcobalamin, methylcobalamin, nicotinic acid, nicotinic acid amide, benzyl nicotinate, calcium pantothenate, sodium pantothenate, pantothenyl alcohol, an ethyl dicarboethoxypantothenate solution in propylene glycol, acetylpantothenyl ethyl ether, pantothenyl ethyl ether, biotin, folic acid, choline, inositol, ascorbic acid, sodium ascorbate, ascorbyl stearate, ascorbyl palmitate, ascorbyl dipalmitate and the like; astringents such as zinc oxide, calamine, aluminium sulfate, lead acetate, bismuth subnitrate, bismuth subgallate, tannic acid, zirconium chloride/oxide, chlorohydroxyaluminium allantoin, dihydroxyaluminium allantoin, aluminium hydroxychloride, zinc chloride, aluminium chloride, ferric chloride, aluminium bromochloride, aluminium phenolsulfonate, aluminium naphthalinesulfonate, dried aluminium potassium sulfate, zinc para-phenolsulfonate and the like; UV absorbers such as urocanic acid, 2-ethoxyethyl-4-methoxycinnamate, ethyl paraaminobenzoate, 2-(2-hydroxy-5-methylphenyl)benzotriazole, 2-hydroxy-4-methoxybenzophenone and the like; metal ion blocking agents such as disodium EDTA, sodium citrate, sodium polyphosphate, sodium metaphosphate, gluconic aid and the like; hypnotics and sedatives such as barbital, thiopental, chloralhydrate, potassium bromide and the like; ataractic and hallocinogenic drugs and antiepileptics such as chlorpromazine, reserpine, chlordiazepoxide and the like; antiparalytic agents such as chlorzoxazone, levodopa and the like; cardiotonics such as digitoxin, digoxin and the like; antiarrhythmic agents such as procainamide hydrochloride, propranolol hydrochloride, lidocaine hydrochloride, indenolol hydrochloride and the like; coronary vasodilators such as dipyridamol, amyl nitrite, nitroglycerin, isosorbitol nitrate and the like; blood pressure depressants such as reserpine, guanetidine sulfate and the like; anti-itching agents such as ichthammol, wood tar, camphor, thymol, diphenhydramine, chlorpheniramine, prometazine hydrochloride, N-ethyl-o-crotonotoluiidide and the like; rubefacients and vesicants such as cantharis, capsicum tincture, ichthammol, terpentine oil, bismuth gallate and the like; skin softeners such as purified sulfur, precipitated sulfur, salicylic acid, urea and the like; sudor inhibitors such as aluminium chloride, aluminium sulfate, aluminium acetate, aluminium phenolsulfonate, sodium perborate and the like; agents for hair such as selenium disulfide, alkylisoquinolinium bromide, zinc pyrithione, biphenamine, thianthol, cantharis tincture, ginger tincture, capsicum tincture, potassium bromate, sodium bromate, carprofen, acetylcholine chloride, pilocarpine chloride, vitamin A and the like; and prostagladins.

The external medicine composition of the invention should preferably comprise 0.5 to 30 wt %, more preferably 1 to 20 wt %, (hereinafter referred to simply as %) of the dialkyl phosphate. The amount of the medically effective ingredients depends greatly on the expectation of development of the efficacy and the kind of agent and is preferably in the range of 0.01 to 20%. The ratio by weight of the dialkyl phosphate and the medical ingredient is generally in the range of 20/1 to 1/10, preferably 10/1 to 1/5.

The external medicine composition of the invention may be in the form of preparations which are directly applied to the skin, i.e. ointment, lotion spray, liniment, pasta, cataplasm and the like. Moreover, the composition may be used as skin cosmetics, hair cosmetics and detergents for tablewares.

If the external medicine composition of the invention is used as a liquid, a dialkyl phosphate and a medical ingredient are suspended in a solvent such as water or water-ethanol, followed by agitating by irradiation of ultrasonic wave or by physical force exerted, for example, from a homogenizer, thereby obtaining a uniform solution. If the ultrasonic wave is used, the solution of the mixture becomes a vesicular solution in view of the properties of dialkyl phosphates. The external medicine composition of the invention may be in the form of a gel or a liquid crystal. Although not limited to the vesicular solution, the external medicine composition lowers in viscosity when subjected to the ultrasonic treatment, with the advantage that it becomes easy to handle on use.

The external medicine composition of the invention is harmless against the skin and ensures high percutaneous absorption of medical ingredients. This mechanism is not known but it is considered that the dialkyl phosphate in the composition has the ability of promoting the absorption of the medical ingredient.

The external medicine composition of the invention can remarkably improve the absorption of the medical ingredient in the skin as will become apparent from examples. Accordingly, in order to obtain the same pharmaceutical effect as in prior art, it is sufficient to use the medical ingredient at a lower concentration with an attendant advantage that the side effect of medical ingredients may be mitigated.

The present invention is described by way of examples.

EXAMPLE 1

Ten grams of didodecyl phosphate arginine salt and 5 g of methyl salicylate were weighed, to which purified water was added so as to make a total weight of 100 g. Thereafter, the mixed suspension was maintained at 50° C. and allowed to stand until the content was gelled. Subsequently, the gel was irradiated with an ultrasonic wave of 26 kHz and 100 W to obtain an external agent of methyl salicylate.

EXAMPLE 2

The percutaneous absorption of the methyl salicylate external agent of Example 1 was determined according to the following method. A male white rabbit having a body weight of about 2.5 kg was fixed on the backside up. The rabbit was cropped by means of electric clippers on the abdominal portion thereof, after which 1 g of the sample (having a methyl salicylate content of 50 mg) was applied onto the outfree skin in an area of about 30 cm². 0.5, 1.0, 1.5, 2.0, 3.0 and 5.0 hours after the application, the blood was sampled. The content of methyl salicylate in the blood was measured, after conversion into salicylic acid, by an ordinary method using a high pressure liquid chromatography. For control, methyl salicyclate (50 mg) and 1 g of commercially sold methyl salicylate ointment (having a methyl salicylate content of 50 mg) were used. The results are shown in FIG. 1.

As will be seen from FIG. 1, the composition of the invention acts to significantly enhance the absorption of methyl salicylate.

EXAMPLE 3

10 g of ditetradecylphosphate arginine salt and 1 g of hydrocortisone acetate were weighed, to which purified water was added to make 100 g of a suspension. Thereafter, the suspension was allowed to stand on a water bath of 50° C. until the content become gelled. Then, the suspension was irradiated with an ultrasonic wave of 26 kHz and 100 W to obtain a hydrocortisone acetate external agent.

EXAMPLE 4

The anti-inflammatory effect of the hydrocortisone acetate external agent of Example 2 was determined by a method of measuring the inhibitory rate of carrageenin edema using rats. Wister male rates (having a body weight of about 150 g and one group consisting of 10 rats) were each injected with 0.1 ml of an aqueous carrageenin 1% physiological saline solution at the foot pad, immediately followed by application of 50 mg of the sample. The sample was removed every 1 hour and the volume of the foot was measured, after which the sample was again applied in an amount of 50 mg. The results are shown in FIG. 2. For control, a commercially sold steroid ointment containing 1% hydrocortisone acetate was used.

EXAMPLE 5

500 mg of nitroglycerin was added to 5 g of ditetradecyl phosphate lysine salt, to which 95 g of purified water was added, followed by agitating to obtain an opaque gel-like composition. This composition was maintained at 50° C. and irradiated with an ultrasonic wave of 20 kHz and 100 W, by which the viscosity was lowered to obtain a nitroglycerin external agent.

EXAMPLE 6

2 g of lidocaine hydrochloride was added to 8 g of dihexadecyl phosphate arginine salt, to which 90 g of purified water, followed by agitating to obtain an opaque gel-like composition. The composition was maintained at 50° C. and irradiated with an ultrasonic wave at 25 kHz and 100 W, by which the viscosity was lowered to obtain a lidocaine hydrochloride external agent.

What is claimed is:

1. A medical composition for external application which is capable of being percutaneously absorbed in high efficiency, which comprises an amount of a medically effective ingredient sufficient to produce a medical effect upon application to the skin, and a dialkyl phosphate of the formula (I):

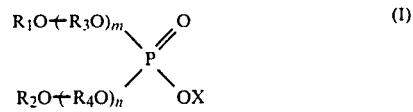

in which $R_1$ and $R_2$ independently represent a hydrocarbon group having a 6-24 carbon atoms, $R_3$ and $R_4$ independently represent a hydrocarbon group having 2 to 6 carbon atoms, m and n independently represent a value of from 0 to 20, and X represents a hydrogen atom, or an alkali metal, ammonium, alkanoylammonium having two or three carbon atoms, alkylammonium having from 1 to 4 carbon atoms, a basic amino acid or morpholine.

2. The medical composition of claim 1, wherein X represents a hydrogen atom or an alkaline metal.

3. The medical composition of claim 1, wherein the sum of m+n is in the range of from 0 to 10.

4. The medical composition of claim 3, wherein both m and n are zero.

5. The medical composition of claim 1, wherein said dialkyl phosphate is selected from the group consisting of didecyl phosphate arginine salt, didodecyl phosphate arginine salt, ditetradecyl phosphate arginine salt, dihexadecyl phosphate arginine salt, dioctadecyl phosphate arginine salt, dieicosyl phosphate arginine salt, didecyl phosphate lysine salt, didodecyl phosphate lysine salt, ditetradecyl phosphate lysine salt, dihexadecyl phosphate lysine salt, dioctadecyl phosphate lysine salt, and dieicosyl phosphate lysine salt.

6. The medical composition of claim 1, wherein said dialkyl phosphate comprises 0.5 to 30 wt. % of the total medical composition.

7. The medical composition of claim 6, wherein said dialkyl phosphate comprises 1 to 20 wt. % of the total medical composition.

8. The medical composition of claim 1, wherein said medically effective ingredients comprise 0.01 to 20 wt. % of the total medical composition.

9. The medical composition of claim 1, wherein the ratio by weight of the dialkyl phosphate to the medical ingredient is in the range of 20/1 to 1/10.

10. The medical composition of claim 9, wherein the ratio by weight of the dialkyl phosphate to the medical ingredient is in the range of 10/1 to 1/5.

11. The medical composition of claim 1, wherein said one or more medically effective ingredient for external application is selected from the group consisting of anodynes and anti-inflammatory agents, adrenocortical hormones, hormones, antiseptics and sterilizers, antihistaminic agents, antifungal agents, vitamins, astringents, UV absorbers, metal ion blocking agents, hypnotics and sedatives, ataractic and hallucinogenic drugs, antiepileptic, antiparalytic agents, cardiotonics, antiarrhythmic agents, coronary vasodilators, blood pressure depressants, anti-itching agents, rubefacients and vesicants, skin softeners, odor inhibitors, hair agents and prostaglandins.

* * * * *